United States Patent [19]

Kress

[11] Patent Number: 4,624,671
[45] Date of Patent: Nov. 25, 1986

[54] METHOD OF SIZING AND IMPLANTING BREAST PROSTHESIS

[76] Inventor: Donald W. Kress, 27 Forest Rd., Wheeling, W. Va. 26003

[21] Appl. No.: 624,354

[22] Filed: Jun. 25, 1984

[51] Int. Cl.⁴ .................... A61F 2/12; G01F 17/00
[52] U.S. Cl. ................................. 623/8; 128/1 R; 73/149
[58] Field of Search ............... 3/1, 36; 128/1 R, 774, 128/778; 73/149

[56] References Cited

U.S. PATENT DOCUMENTS

| | | | |
|---|---|---|---|
| 3,227,154 | 1/1966 | Cook | 128/778 |
| 3,416,160 | 12/1968 | Arion | 3/36 |
| 3,600,718 | 8/1971 | Boone | 3/36 |
| 4,024,856 | 5/1977 | Kirianoff | 3/36 |
| 4,095,295 | 6/1978 | Lake | 3/36 |
| 4,143,428 | 3/1979 | Cohen | 3/36 |
| 4,328,811 | 5/1982 | Fogarty | 128/774 |

Primary Examiner—Richard J. Apley
Assistant Examiner—David J. Isabella
Attorney, Agent, or Firm—Webb, Burden, Robinson & Webb

[57] ABSTRACT

A method of sizing a breast prosthesis and implanting an accurately sized breast prosthesis is disclosed. The method invovles implanting an empty, inflatable elastomeric balloon in a breast, filling the balloon with a liquid to a desired size, measuring the amount of liquid in the filled balloon, removing the liquid from the balloon, and removing the empty balloon from the breast. A final breast prosthesis is sized in accordance with the amount of liquid that was in the filled balloon. The properly sized final breast prosthesis is then implanted into the breast.

25 Claims, 1 Drawing Figure

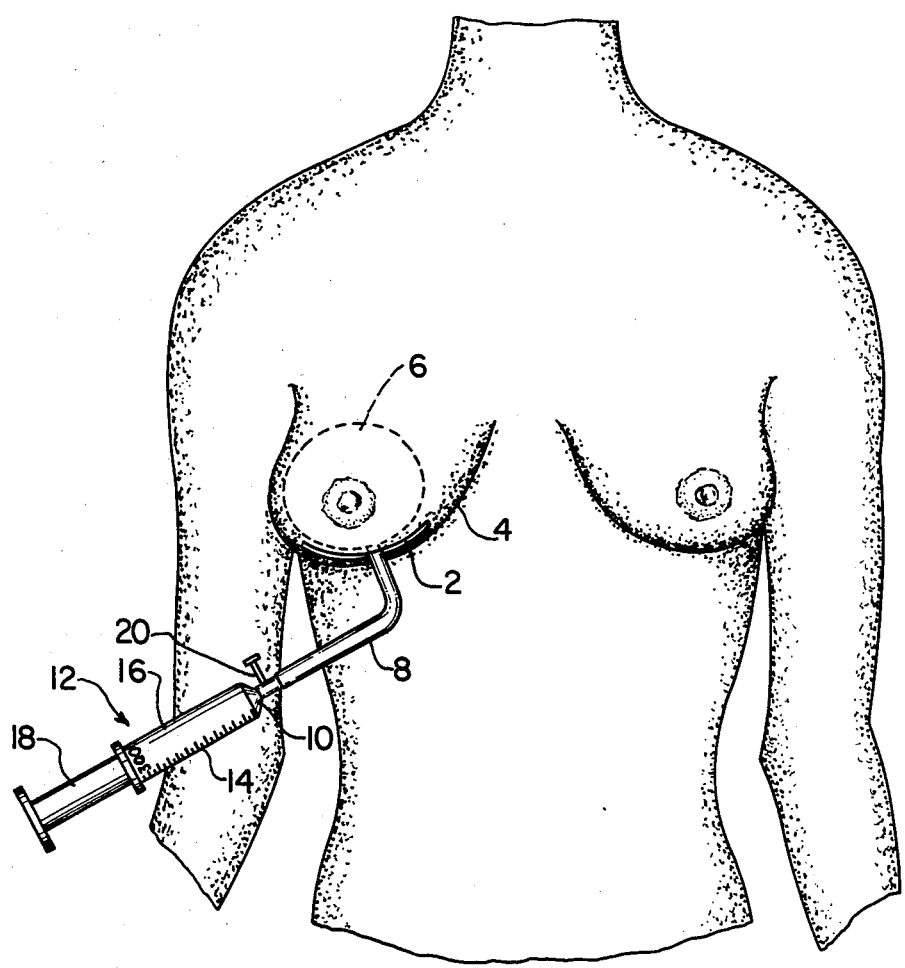

METHOD OF SIZING AND IMPLANTING BREAST PROSTHESIS

BACKGROUND OF THE INVENTION (1) Technical Field of the Invention

This invention relates to mammaplasty augmentation and more particularly, to a method of accurately sizing a breast prosthesis prior to implantation and to a method of implanting an accurately sized breast prosthesis.

(2) Description of the Prior Art

It is well known in the field of plastic surgery that a human breast may be augmented or enlarged, either for medical or cosmetic reasons, with prosthetic implants. In one common surgical procedure, an incision is made through the skin along the bottom of the patient's breast, the breast tissue is elevated, and a pocket or cavity is formed between the breast tissue and the underlying chest wall. If the breast tissue or mammary glands have been previously removed during a mastectomy, then the cavity is present between the patient's skin and chest wall. The surgeon has a set of premanufactured, sterilizable implants sized and marked in volumes from 125 cc to 325 cc in 25 cc increments. The surgeon selects one of the sterilizable implants, inserts it into place through the incision, and determines by visual and manual inspection if the implant is of the proper or desirable size. If not, the surgeon removes the implant, selects a second implant of another size, inserts the second implant into place, and again determines if the implant is of the proper size. This procedure is repeated until the surgeon has, by trial and error, determined the necessary size for the implant. Then the sterilizable implant is removed, a final premanufactured implant, sized by the above method, is inserted in place and the incision is closed by suturing or the like. The final implant is typically an elastomeric silicone bag containing a saline solution or a silicone gel.

This procedure has the disadvantage that the determination of the final implant size is basically a trial and error procedure and requires that an implant be inserted into the patient and then removed several times or more before the final implant is inserted in place. Such a procedure is lengthy to perform and may cause additional damage to the patient due to the repeated insertion and removal of the sterilizable implants.

U.S. Pat. No. 4,024,856 discloses a method and apparatus for measuring the size of a breast relative to a predetermined volume and for determining the difference in size between a woman's right breast and left breast. A template of predetermined size and shape, larger than the patient's breast, is placed over each breast and a measured amount of fluid is injected between the template and the breast. By measuring the differences between the known volume of the template and the known volume of liquid injected, the breast size may be determined and an implant sized accordingly. However, this apparatus and method is quite cumbersome and messy and requires the construction of a template corresponding to the desired final size and shape of the breast. In addition the final appearance of the patient's breast will be known only after a breast implant is finally inserted.

It is also known in the art to implant an empty elastomeric silicone balloon in a patient's breast, inflate the balloon through a filler tube with a saline solution or similar liquid until the desired size is reached, and then seal off the opening to the now implanted and filled balloon. Such devices and methods are disclosed, for example, in U.S. Pat. Nos. 4,143,428; 4,095,295; 3,600,718; and 3,416,160. Once the balloon is filled it must be sealed by plugging or otherwise closing off the filler tube. Such an implant is not as reliable as a permanently sealed implant and leaks or other problems may arise after the surgery is completed.

Accordingly, it is an object of the present invention to accurately determine the size of a desired breast implant without a repeated trial and error procedure and, thereby, enable a final implant to be inserted without the necessity of sealing the final implant.

SUMMARY OF THE INVENTION

A method of accurately sizing a breast prosthesis prior to implantation which includes the steps of implanting an empty, inflatable elastomeric balloon in a breast, filling the balloon with a liquid to a desired size, measuring the amount of liquid in the filled balloon, removing the liquid from the balloon, and removing the empty balloon from the breast. A final breast prosthesis is sized in accordance with the amount of liquid in the filled balloon. One incision may be made along the bottom portion of the breast which permits the balloon to be inserted behind the breast and later withdrawn, and which permits the final breast prosthesis to be implanted.

The balloon is made of a nontoxic, flexible plastic material which is impermeable to liquid, such as a silicone elastomer. The balloon may be filled by a standard syringe connected thereto, preferably with a filler tube, and the amount of liquid in the filled balloon is determined by observing the extent of travel of the syringe stem within the syringe barrel. The balloon is preferably filled with a saline solution. The final breast prosthesis may be an elastomeric silicone bag containing a saline solution or a silicone gel.

BRIEF DESCRIPTION OF THE DRAWING

FIG. 1 is a front view of the upper female torso showing a silicone balloon inserted and being filled in accordance with the present invention.

DESCRIPTION OF THE PREFERRED EMBODIMENTS

A method of accurately sizing a breast prosthesis prior to implantation in accordance with the present invention is set forth with reference to FIG. 1. Initially, an incision 2 is made through the skin along the bottom portion of the patient's breast 4 which is to be augmented by surgery. The incision is made of sufficient length and depth to accept a final, filled breast prosthesis or implant (not shown in FIG. 1). In accordance with procedures well-known in the art, the breast tissue is elevated and a pocket or cavity is formed between the breast tissue and the underlying chest wall. If the breast tissue has previously been removed during a mastectomy, the cavity is formed between the skin of the breast 4 and the chest wall.

An empty or collapsed, elastomeric balloon 6, preferably including a filler tube 8 attached thereto, both of which have been properly sterilized, is inserted through the incision 2 and into the cavity behind the breast 4 as shown in FIG. 1. The filler tube 8 is connected to a standard syringe 12 via a nipple outlet 10. The syringe 12 includes a barrel portion 16 and a stem portion 18 slidably mounted within the barrel portion 16. The barrel portion 16, which is preferably clear, is marked with a plurality of volume markings 14. The outlet 10 of the syringe 12 may be provided with an on/off valve 20, such as a butterfly valve, in order to more accurately control the flow of fluid from the syringe 12.

The syringe 12 is initially filled with a suitable liquid, such as a saline solution, and then the filler tube 8 is connected to the nipple outlet 10. Then the valve 20 is opened and by pressing down on the stem 18 the liquid is forced from the barrel 16 of the syringe 12, through the filler tube 8, and into the balloon 6. The balloon 6 will then gradually begin to fill with the liquid. The liquid is forced into the balloon 6 until it has been inflated to the desired size. That the desired size of the balloon 6 has been reached is determined by the surgeon visually and manually inspecting the augmented size of the breast 4 under treatment. At that point, no further force is applied to the stem 18, the on/off valve 20 may be closed, and no further liquid is forced into the balloon 6.

By observing the extent of travel of the stem 18 within the barrel 16 of the syringe 12 and with reference to the volume markings 14, the surgeon can determine the amount of liquid injected into the balloon 6. With this knowledge, the surgeon knows exactly the size of breast implant needed and can make the selection of a final implant accordingly.

Once the size of the final implant has been determined, the liquid in the balloon 6 is removed, either by withdrawing the stem 18 to its original position or by disconnecting the filler tube 8 from the syringe 12 and letting the liquid drain out. The now collapsed balloon 6, along with the filler tube 8, is removed from the cavity through the incision 2. The surgeon then takes the final, permanent breast implant, which has previously been precisely sized as described above, and inserts this implant through the incision 2 and into the cavity formed behind the breast 4. The surgical procedure is completed by closing the incision 2 with sutures or the like.

The balloon 6 when deflated is pancake-shaped, on the order of, for example, four inches in diameter, and when inflated assumes the shape of a human breast. The balloon 6 is composed of any nontoxic, flexible plastic material impermeable to liquid, such as a medical grade of silicone elastomer or an organo siloxane copolymer. When formed of a silicone elastomer, the balloon 6 has a wall thickness of, for example, 0.012–0.20 inch (0.3–0.5 mm) and weighs from 8 to 16 grams. The filler tube 8 may be approximately ⅛ inch in outer diameter, and 3/32 inch in inner diameter and extend outwardly in a radial direction from the periphery of the balloon 6.

A preferred fluid for inflating the balloon is a normal saline solution, designated N/saline, which consists of 0.9 percent NaCl dissolved in water. It will be understood, however, that many other types of liquids may be used for the purposes of the present invention, the principal requirement being that the solution is nontoxic, does not substantially react with the body fluids, and has a relatively low viscosity so that it can be pumped freely into the balloon 6 through the filler tube 8 without drying up or crystallizing so as to stop up the tube 8.

The syringe 12 typically has a volume of 300–400 cc and the syringe 12 is filled with a saline solution having a volume between 300–400 cc, which volume is sufficient for completely filling or inflating the balloon 6 without the necessity of detaching and refilling the syringe 12. In addition, the surgeon will know precisely how much saline has been injected into the ballon 6 without the need of counting and keeping track of the number of times the syringe 12 is refilled. Since the standard final breast implants range from 125 cc to 325 cc in size, a 300–400 cc syringe will be appropriate for most applications. For a different size balloon 6 and, consequently, a different size final implant, a different size syringe may be used. Although the invention has been described using a syringe 12, any other apparatus for injecting liquid into the balloon 6 may be utilized as long as the amount of liquid injected can be precisely measured.

The final implant may be any of the commercially available breast prostheses, typically an elastomeric silicone bag containing a saline solution or a silicone gel.

Having described presently the preferred embodiments of the invention, it is understood that it may be otherwise embodied within the scope of the appended claims.

I claim:

1. A method of sizing a breast prosthesis comprising the steps of
   (a) implanting an empty, inflatable elastomeric balloon in a breast;
   (b) filling the balloon with a liquid to a desired size;
   (c) measuring the amount of liquid in the filled balloon;
   (d) removing the liquid from the balloon; and
   (e) removing the empty balloon from the breast.

2. The method of claim 1 wherein the balloon is made of a nontoxic, flexible plastic material impermeable to liquid.

3. The method of claim 2 wherein the balloon is made of a silicone elastomer.

4. The method of claim 1 wherein the balloon is filled by a syringe connected thereto.

5. The method of claim 4 wherein a filler tube is connected between the syringe and the balloon.

6. The method of claim 4 wherein the syringe includes a barrel and a stem slidably mounted within the barrel and wherein the amount of liquid in the filled balloon is measured by observing the extent of travel of the stem within the barrel.

7. The method of claim 1 wherein the balloon is filled with a saline solution.

8. A method of implanting a precisely sized breast prosthesis comprising the steps of
   (a) implanting an empty, inflatable elastomeric balloon in a breast;
   (b) filling the balloon with a liquid to a desired size;
   (c) measuring the amount of liquid in the filled balloon;
   (d) sizing a final breast prosthesis in accordance with the amount of liquid in the filled balloon;
   (e) removing the liquid from the balloon;
   (f) removing the empty balloon from the breast; and
   (g) implanting the final breast prosthesis.

9. The method of claim 8 wherein the balloon is made of a nontoxic, flexible plastic material impermeable to liquid.

10. The method of claim 9 wherein the balloon is made of a silicone elastomer.

11. The method of claim 8 wherein the balloon is filled by a syringe connected thereto.

12. The method of claim 11 wherein a filler tube is connected between the syringe and the balloon.

13. The method of claim 11 wherein the syringe includes a barrel and a stem slidably mounted within the barrel and wherein the amount of liquid in the filled balloon is measured by observing the extent of travel of the stem within the barrel.

14. The method of claim 8 wherein the balloon is filled with a saline solution.

15. The method of claim 8 wherein the final breast prosthesis is an elastomeric silicone bag containing a saline solution.

16. The method of claim 8 wherein the final breast prosthesis is an elastomeric silicone bag containing a silicone gel.

17. A method of accurately sizing a breast prosthesis and implanting the same comprising the steps of
   (a) making an incision along the bottom portion of a breast;
   (b) inserting an empty, inflatable elastomeric balloon through the incision and into a cavity behind the breast;
   (c) inflating the balloon with a liquid to a desired size;
   (d) measuring the amount of liquid in the inflated balloon;
   (e) selecting a final breast prosthesis as determined by the amount of liquid in the inflated balloon;
   (f) deflating the balloon;
   (g) withdrawing the empty balloon from the cavity and through the incision;
   (h) inserting the final breast prosthesis through the incision and into the cavity; and
   (i) surgically closing the incision.

18. The method of claim 17 wherein the balloon is made of a nontoxic, flexible plastic material impermeable to liquid.

19. The method of claim 18 wherein the balloon is made of a silicone elastomer.

20. The method of claim 17 wherein the balloon is filled by a syringe connected thereto.

21. The method of claim 20 wherein a filler tube is connected between the syringe and the balloon.

22. The method of claim 20 wherein the syringe includes a barrel and a stem slidably mounted within the barrel and wherein the amount of liquid in the filled balloon is measured by observing the extent of travel of the stem within the barrel.

23. The method of claim 17 wherein the balloon is filled with a saline solution.

24. The method of claim 17 wherein the final breast prosthesis is an elastomeric silicone bag containing a saline solution.

25. The method of claim 17 wherein the final breast prosthesis is an elastomeric silicone bag containing a silicone gel.

* * * * *